United States Patent
Nguyen et al.

(10) Patent No.: US 9,395,562 B1
(45) Date of Patent: Jul. 19, 2016

(54) METHOD AND APPARATUS FOR EYE AND EYEWEAR CHARACTERISTICS MEASUREMENT

(71) Applicants: Hoa Nguyen, Cedar Hill, TX (US); Sameer Cholayil, Fort Worth, TX (US); Phuong Pham, Arlington, TX (US); Cuong Manh Nguyen, Arlington, TX (US)

(72) Inventors: Hoa Nguyen, Cedar Hill, TX (US); Sameer Cholayil, Fort Worth, TX (US); Phuong Pham, Arlington, TX (US); Cuong Manh Nguyen, Arlington, TX (US)

(73) Assignee: PERFECT SQUARES, INC., Cedar Hill, TX (US)

( * ) Notice: Subject to any disclaimer, the term of this patent is extended or adjusted under 35 U.S.C. 154(b) by 0 days.

(21) Appl. No.: 14/680,871

(22) Filed: Apr. 7, 2015

(51) Int. Cl.
*A61B 3/10* (2006.01)
*G02C 13/00* (2006.01)
*A61B 3/00* (2006.01)
*A61B 3/14* (2006.01)

(52) U.S. Cl.
CPC ............ *G02C 13/005* (2013.01); *A61B 3/0025* (2013.01); *A61B 3/14* (2013.01)

(58) Field of Classification Search
CPC ........ A61B 5/0077; A61B 3/14; A61B 3/145; A61B 3/12
USPC ......... 351/204, 246, 200, 206, 208, 209, 210; 348/49
See application file for complete search history.

(56) References Cited

U.S. PATENT DOCUMENTS

| | | | |
|---|---|---|---|
| 8,840,247 B2 * | 9/2014 | Kratzer ................. | A61B 3/111 351/204 |
| 2014/0152956 A1 * | 6/2014 | Silva ..................... | A61B 3/111 351/204 |
| 2014/0240470 A1 * | 8/2014 | Dias Da Silva ...... | G02C 13/005 348/49 |
| 2014/0354947 A1 * | 12/2014 | Hsieh .................. | G02C 13/003 351/204 |

* cited by examiner

Primary Examiner — Hung Dang

(57) ABSTRACT

A method and apparatus for contactless measurement of the characteristics of patients' eyes and eyewear without using any reference device for scaling measurements. The non-contact system comprises of a measurement device having an array of proximity sensors for contactless distance measurement, which is embracing a mobile device having a digital camera, a processor, gyroscope or 3-axis accelerometer sensors, and wireless transceivers. The wireless transceivers support fast and real-time communication between the mobile device and the measurement device. The mobile device is configured to obtain information of distance between the patient face the measurement device at the same time as the digital camera is capturing images of the patient. Such distances assist the processor of the mobile device to re-construct actual eye and eyewear characteristics from the captured image of the digital camera. The built-in gyroscope sensors may be used to correct errors caused by inadequate orientation of the patient's face and/or the mobile device. The method thus enables fast, accurate and reference less measurement, and reduces the responsibilities of users.

15 Claims, 9 Drawing Sheets

METHOD AND APPARATUS FOR EYE AND EYEWEAR CHARACTERISTICS MEASUREMENT

CROSS REFERENCE TO RELATED APPLICATIONS

Not Applicable

FEDERALLY SPONSORED RESEARCH

Not Applicable

SEQUENCE LISTING OR PROGRAM

Not Applicable

FIELD OF THE INVENTION

The invention presented here relates to field of eye and eyewear characteristics measurement at an opticians office so as to best fit the patient with eyewear for optimal optical performance and comfort of the eyewear.

BACKGROUND OF THE INVENTION

Characteristics of the eye in combination with eyewear such as, distance between the left and right eye pupils known as pupillary distance (PD); frame wraps around the face of its wearer at the wrap angle, draw a line through the 2 edges of left rim and draw another line for right rim, the lesser of the two angles between these two lines is known as the wrap angle (WA); distance between center of pupil and bottom of the lens known as segment height (SH); angle between vertical and the plane of the lens known as the pantoscopic tilt or angle (PA); and distance between pupil and back side of the lens know as vertex distance (VD), are critical pieces of information for designing eyewear for patients wearing eyeglass. Traditional ways use rulers or protractors to manually carry out such measurements. Automatic methods may use a digital camera to capture patient faces and a computerized system to calculate eye characteristics based on the capture images. The computerized system needs a scale factor to convert information extracted from the captured image into the actual distance and/or angles.

Prior art, U.S. Pat. No. 6,535,223B1, titled "METHOD AND SYSTEM FOR DETERMINING PUPILTARY DISTANT AND ELEMENT HEIGHT" uses a monetary coin of known dimensions held on chin as the reference object to scale the distances measured within points in the captured image. This is not something easy to use and patients getting their measurements taken do not enjoy the experience. Further there is no correction for the errors introduced in the reference coin part of the image due to tilt and yaw. Reference error translates to a bigger error in the measurement.

Prior art, U.S. Pat. No. 5,592,248 titled "COMPUTERIZED METHOD FOR FITTING EYEGLASSES" uses a camera on trips and patients chin fixed on a fixture at fixed distance to know the distance from the camera to the chin as reference. The deficiency is that the temple of the patient can move back and forward a few mm's from the chin distance introducing errors in the reference distance. The camera on tripod may have yaw error if not carefully inspected any time. The tilt or yaw error due to face tilt and yaw also introduces errors in the measurement. Reference error translates to a bigger error in the measurement.

Prior art, patent publication N0:US2013/0278895A1 describes using a pair of laser to draw reference objects on the face of the patient to get reference measurement. The laser system needs individual calibration or there will be errors in the reference objects due to manufacturing variations.

Contemporary measurement systems still use reference scales or devices with known information to obtain the scale factors. The reference devices may be worn by the patients and are visible on the captured image. Some systems are able to generate reference points with the known distance of the patient's face to replace the reference devices. Such measurement methods create distractions or unintended errors if the patient face is not correctly positioned and aligned with the measurement devices. The users are requested to train or ask the patient to obey instruction step by step.

Developing a quick and reference object free measurement method to extract eye characteristics is a crucial task. The invention aims to remove the need of reference devices or scales while keeping measurements valid with minimum errors. The reference object free measurement technique decreases measurement time, reduces the responsibilities of the users, and guarantees less stress for the patient during measurement.

BRIEF SUMMARY OF THE INVENTION

The method disclosed herein implements an array of proximity sensors placed in a measurement device that is attached to a mobile device (e.g. a smartphone or a tablet) to quickly obtain eye characteristics of a patient in front of its camera. In these particular embodiments, a measurement device comprises of an array of three proximity sensors which are implemented for distance measurement and yaw rotation angle of the face. These sensors are aligned and projected to the forehead of the patient. In some embodiments, the proximity sensors of the measurement device could be arranged and re-ordered to project to different parts of the face. In other embodiments, numbers of sensors of the measurement device may be varied to obtain higher precision in measuring the distance from the face. In one embodiment of the invention, the proximity sensor may work on principle of time-of-flight laser distance measurement. The advantage of this sensor being that, its distance accuracy is independent of ambient lighting and texture of the surface. Ultrasonic time-of-flight proximity sensor may similarly be used in another embodiment of the invention for similar advantages as that of laser time-of-flight proximity distance sensor.

In an illustrative embodiment, the measurement device was mechanically attached to the mobile device that contains a built-in camera and a Bluetooth transceiver. Mechanical clips support wide range of the mobile devices with various dimensions. Information from the measurement device is continuously transmitted to the mobile device to assist the user in finding the proper position to capture pictures. Once the proper position is found, the mobile device allows the user to capture pictures by a control button. An execution command will be sent to the measurement device to acquire distance of the face in meanwhile. In other embodiments, capture control can be activate by voice through the microphone of the mobile device. In some embodiments, automatic capture can be configured to reduce the user's work once the camera finds the focus points of the patient face.

The position and measurement of the face will be determined based on distance from the camera and three rotation angles roll, pitch and yaw. In an illustrative embodiment, the distance and yaw angle will be calculated based on the information of the array of proximity sensors from the measurement device. The roll and pitch angles were retrieved from the built-in gyroscope sensors of the mobile devices. In other embodiments, the measurement device could integrate its own gyroscope sensors for measuring of roll, pitch and yaw angles. Some other embodiments do not have gyroscope sensors to reduce their dimension with an assumption of known and preset roll, pitch and yaw angles.

In an illustrative embodiment, the array of proximity sensors return distances of three points on the forehead of the patient to the camera. The middle sensor determines the overall distance between the patient and the camera. The left and right sensors will be used to calculate yaw angle of the face. In other embodiments, two proximity sensors project to the forehead while the other one project to the chin of the patient. Average distance of three sensors returns the overall distance between the patient and the camera. Information of the distance to the forehead is used to calculate the yaw angle of the face. In some embodiments, additional proximity sensors will be used for error correction.

Methods for two-way communication between the measurement devices and the mobile device are done using a wireless transceiver. In an illustrative embodiments, commands of executing, capturing, requesting, and sending information are utilizing Bluetooth low-energy protocol. In other embodiments, Wi-Fi communication following standard IEEE 802.11 protocols can be utilized. In some embodiments, near field communication (NFC) can be utilized for the mobile device supporting such communication. Wireless communication between these devices allow to assembly and disassembly easily. A built-in accelerometer sensor of the mobile device could enable sleeping mode of the measurement device to reduce power consumption when it is not in use.

In an illustrative embodiments, the built-in camera of the mobile device is utilized to acquire pictures of the patient wearing a selected frame. The mobile device is able to analyze the capture picture using image processing algorithms. A built-in application (app) is developed to search for the centers of the pupils and determine position of the wearable frame. Measuring distance in terms of the number of pixels including a monocular pupillary distance (PD), a binocular near PD, a monocular near PD, a binocular near PD, a vertex distance, a wrap angle, a pantoscopic tilt will be determined. These actual distances then are re-constructed and calculated based on scaling factors that found from the distance between the patient and the mobile device.

The method and apparatus provide highly accurate and rapid acquisition of eye characteristics while reducing stresses and efforts of the patient during measurement. The innovation method enables free of reference objects or needs of any reference measurement devices attached to eyewear frames or the patient's heads in practical uses.

In an illustrative embodiment, the built-in application have functions to connect to internet server to store information in database, which reduces responsibility of the patients, or request an order of frames and lenses directly to the ophthalmic laboratory, which provides convenience and time-efficient to users.

BRIEF DESCRIPTION OF THE DRAWINGS

The apparatus and method for reference object free contactless detection of eye characteristics are described below. In this description, reference will be made to the accompanying drawings, which are not necessarily drawn to scale, and wherein.

DETAILED DESCRIPTION OF THE INVENTION

Detailed embodiments of the method for reference object free detection of eye characteristic are disclosed herein. It should be understood that the invention may be embodied in many different forms and should not be considered as limited to the embodiments set forth herein. Rather, these embodiments are provided so that this disclosure will be thorough and complete, and will fully convey the scope of the invention to those skilled in the art. Like numbers refer to like elements throughout.

The system design is described in this paragraph. Generally, the measurement method and system disclosed herein compromise of two parts: a mobile device and a measurement device. The mobile device features with a digital camera, wireless transceiver, a computing processor, a gyroscope sensor, accelerometer sensors, and additional components. The mobile device also supports cloud computing infrastructure having wired or wireless connection to servers, database, and/or other computers, and external computer-readable card, for example, secure digital card, or hard drive. A contemporary example of the mobile device is an iPad tablet computer. The measurement device compromises but not limited to array of proximity sensors, a microcontrollers, and a wireless transceiver. The mobile device may support external secure digital card to temporarily store information.

Communications between the mobile device and the measurement device disclosed herein is wireless and bidirectional which allows for mobility, flexibility and durability. In the illustrative embodiments, Bluetooth low-energy is implemented for communication between the mobile device and the measurement devices. The measurement device may support multiple wireless communication protocols that provides flexibility to connect to different types of the mobile devices. The mobile device may support wired or wireless connection to Internet directly or indirectly with other computers to store information in database or share information with ophthalmic laboratory.

Figure 1:
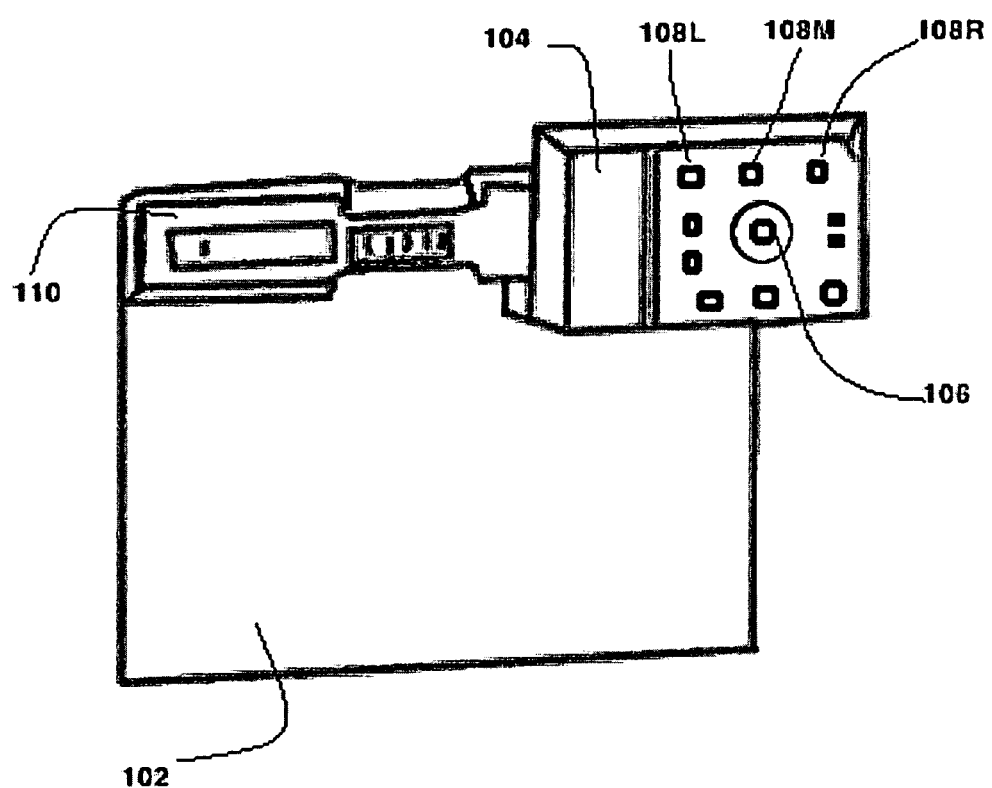
FIG. 1 illustrates a perspective view of a mobile device including a measurement device.

FIG. 1 is an illustrative embodiment, a measurement device 104 is connected with the mobile device 102. The measurement device 104 may be mounted on top of the mobile device 102 and aligned on the top of the digital camera 106 of the mobile device 104 by mechanical clip attachment 110. The mechanical clip attachment 110 is designed with an adjustable length to fit with different dimension of the the mobile device 104. The mechanical clip attachment allows the measurement device 104 removable from the mobile device 102.

The measurement device 104 include array of proximity sensors 108 with fixed and known positions relatively to the digital camera 106. As shown in FIG. 1, three sensors 108L, 108M, 108R are denoted to the one in the left, middle and right, respectively. In an illustrative embodiment, the proximity sensors 108 uses time-to-flight technology allowing to precisely measure distance to the nearest projected object based on the time that infrared light travels back and forth. One example of the proximity sensors 108 is part number VL6180X from STMicroelectronics, a semiconductor manufacturer located in Geneva, Switzerland. The sensor package combine an infrared emitter with operating wavelength of 840 nm, an ambient light sensor, microcontroller, internal memory and support inter-integrated circuit communication with other devices.

Figure 2A:
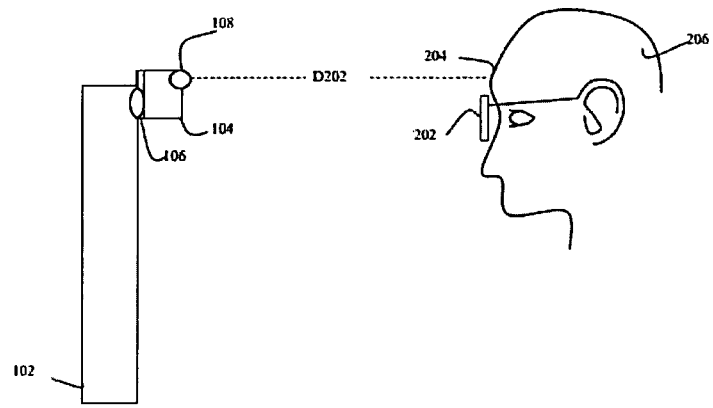
FIG. 2A illustrates a side view of a mobile device including a measurement device.

As illustrated in FIG. 2A, the side view, the embodiment including the mobile device 102 and the measurement device 104 provides a means to contactless measurement of eye and eyewear characteristic of the patient head 206. Measurement distance D202 between the measurement device 104 and the forehead 204 of the patient head 206 is in the range of 100 mm to 130 mm. Within the aforementioned range, the proximity sensors 108 of the illustrative embodiment provide highly precision measurement.

In the illustrative embodiment, the patient 204 may wear a pair of glasses or reference frame 202 for further characterization of eye characteristic such as segment heights for bifocal measurement.

Figure 2B:
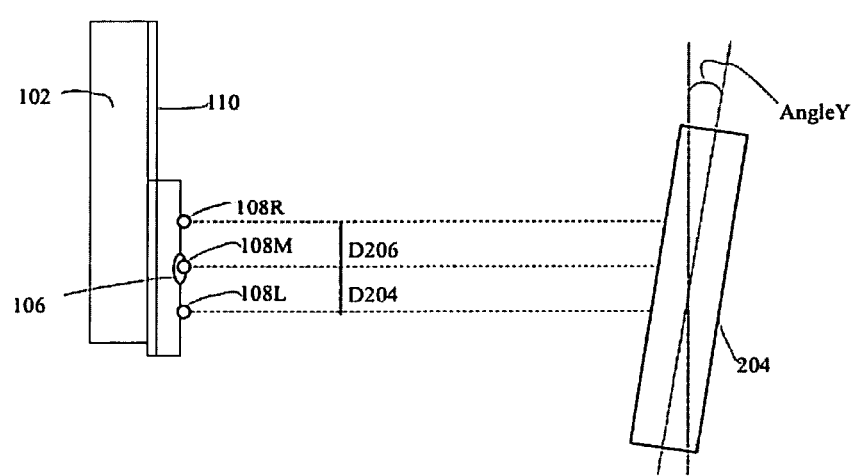
FIG. 2B illustrates a top view of a mobile device including a measurement device.

In the illustrative embodiment FIG. 2B, the array of proximity sensors 108 projects to the forehead 204 of the patient head 206. The sensors 108L, 108M, and 108R are positioned next to each other, aligned horizontally along and parallel with the forehead. The medium distance measured by three sensors 108L, 108M, and 108R provide distance between the measurement device 104 and the forehead 204 of the patient head 206. The yaw angle AngleY is estimated when patient head 206 is not aligned with three proximity sensors.

The spacing distance D204 between the proximity sensors 108L and 108M is set equal to the spacing distance D206 between the proximity sensors 108M and 108R. In the illustrative embodiment, the spacing distances D204 and D206 are 30 mm.

Figure 3A:
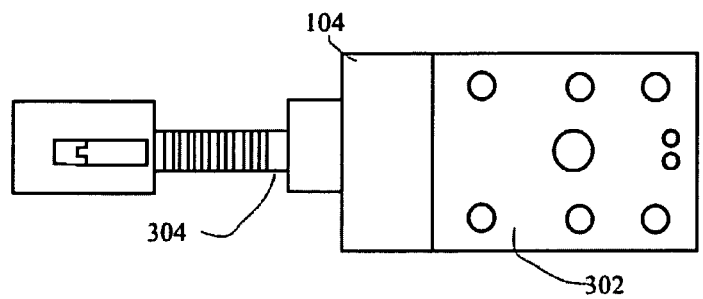
FIG. 3A illustrates a front view of an embodiment of a measurement device.

FIG. 3A, front view, illustrates the structure of the measurement device 104 including a box 302 that is containing electronic components, sensors and power management system; and, an adjustable clamp 304.

Figure 3B:
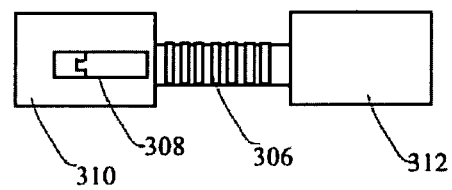
FIG. 3B illustrates a front view of an embodiment of an adjustable clamp of a measurement devices.

FIG. 3B, front view, shows the structure of the adjustable clamp 304 consists of a horizontal bar 306, a mechanical clip 308, a bottom strap 310 and a top strap 312. The horizontal bar 306 is designed to have an array of through holes for locking purposes using the mechanical clip 308. The distance D302 between the bottom strap 310 and the top strap 312 can be adjusted according to the dimension of the mobile device 102 unless the mechanical clip 308 is locked.

In the illustrative embodiment, the horizontal bar 306 is permanently connected to the box 302 and the top strap 312 while the bottom strap 310 is permanently connected to the mechanical clip 308. In some embodiments, the horizontal bar 306 could be designed to permanently attached to the bottom strap. In such cases, the mechanical clip 308 could be connected to the top strap 312. Thus, relative moving between the bottom strap 310 and the top strap 312 is still remained and the distance D302 is still adjustable.

Figure 3C:
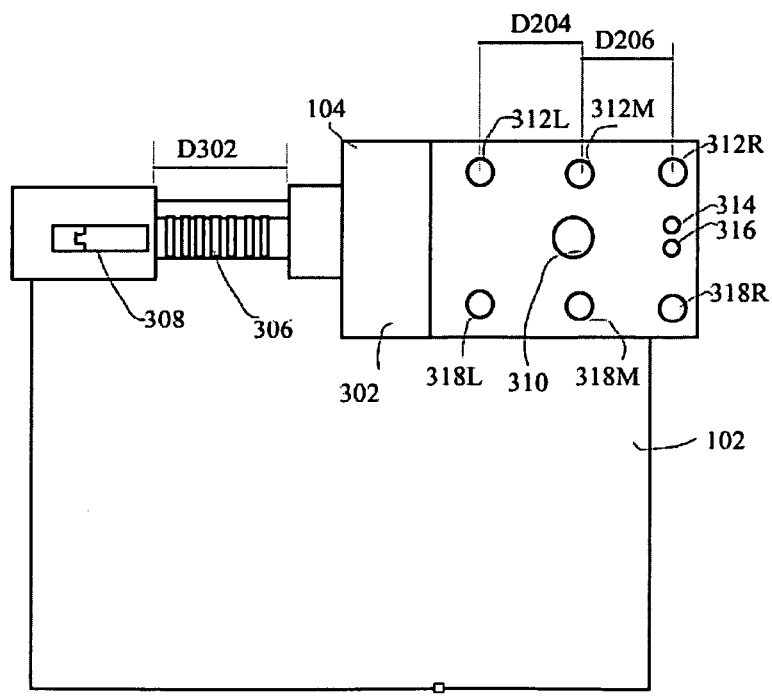
FIG. 3C illustrates a front view of an embodiment of a measurement device with a mobile device.

FIG. 3C, front view, illustrates the measurement device 104 is removably attached to the mobile device 102. The mechanical clip 308 fixes the distance D302 small enough for the measurement device 104 to connect to the mobile device 102. The box 302 includes the camera hole 310 with a diameter of 30 mm for the camera 106 of the mobile device 104. The position of the camera hole 310 may be varied with different embodiments. In the illustrative embodiment, the camera hole 310 is located in the center of the box.

The box 302 includes three sensor holes 312L, 312M, and 312R for the array of proximity sensors 108L, 108M, and 108R, respectively. In other embodiments, the number of the proximity sensors could be more than three in order to obtain higher precision of distance measurement. In an illustrative embodiments, three sensor holes 312 for the proximity sensors 108 are arranged and aligned horizontally. The spacing distance between these sensor holes are D204 and D206. The middle sensor hole 312M is located on top of the camera hole while the other two sensor holes are symmetrically placed on the left and the right sides of the camera. In other embodiments, the camera hole and three sensor holes could be placed horizontally or vertically. In some embodiments, the location of these holes may be different; however, distances between these holes are fixed and well-defined.

In the illustrative embodiment, there are two other holes for light-emitting diodes (LED) 314 and 316 to indicate a charging mode and active mode, respectively. In other embodiments, the number of LEDs may varied that depends on the user requirements.

In the illustrative embodiment, three more holes for additional proximity sensors 318 as indicated in FIG. 3C. The position of these proximity sensors 318 are arranged symmetrically to the proximity sensors 312.

Figure 4:
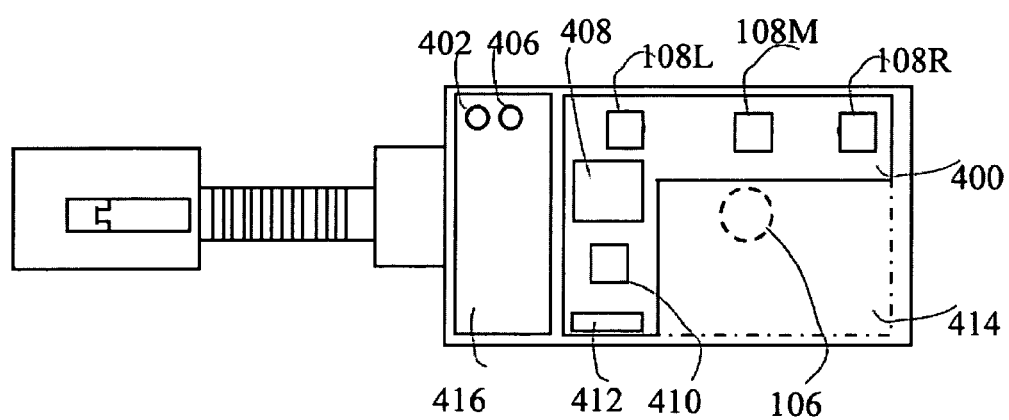
FIG. 4 illustrates a perspective view showing internal components of the measurement device in FIG. 3C.

FIG. 4 shows internal components of an illustrative embodiment of the measurement device 104 compromising of printed circuit board 400 having array of proximity sensors 108, a microcontroller 408, a Bluetooth low-energy transceiver 410 and a radio-frequency antenna 412 for wireless communication. In some embodiments, the microcontroller 408, the Bluetooth low-energy transceiver 410 and the radio-frequency antenna 412 can be re-arranged and placed on the back side of the printed circuit board 400. In other embodiments, the microcontroller 408 integrates the Bluetooth low-energy transceiver 410 in a single system-on-chip integrated circuit, so-called IC, such as nRF51822 or nRF51422 from the semiconductor manufacturer Nordic Semiconductor located in Oslo, Norway.

In the illustrative embodiment, the printed circuit board 400 has an L-shape with a length of 108 mm, a long width of 51 mm and a short width of 23 mm. The imaginary trimming-off area 414 of the L-shape 400 is illustrate the position of the camera 106 of the mobile device 102 when the measurement device 104 connect to the mobile device 102. In other illustrative embodiments, the printed circuit board 400 may have various dimensions, wherein the array of proximity sensors 108, the microcontroller 408, the Bluetooth low-energy transceiver 410, and the radio-frequency antenna 412 could be housed. However, the spacing distances of the two adjacent sensors, for example distance between 108L and 108M, and distance between 108M and 108R are still remained of D204 and D206, respectively.

As illustrated in FIG. 4, the printed circuit board 400 compromises of a power switch button 402 and reset switch button 404. The printed circuit board 400 also include battery holder 416.

Figure 5A:
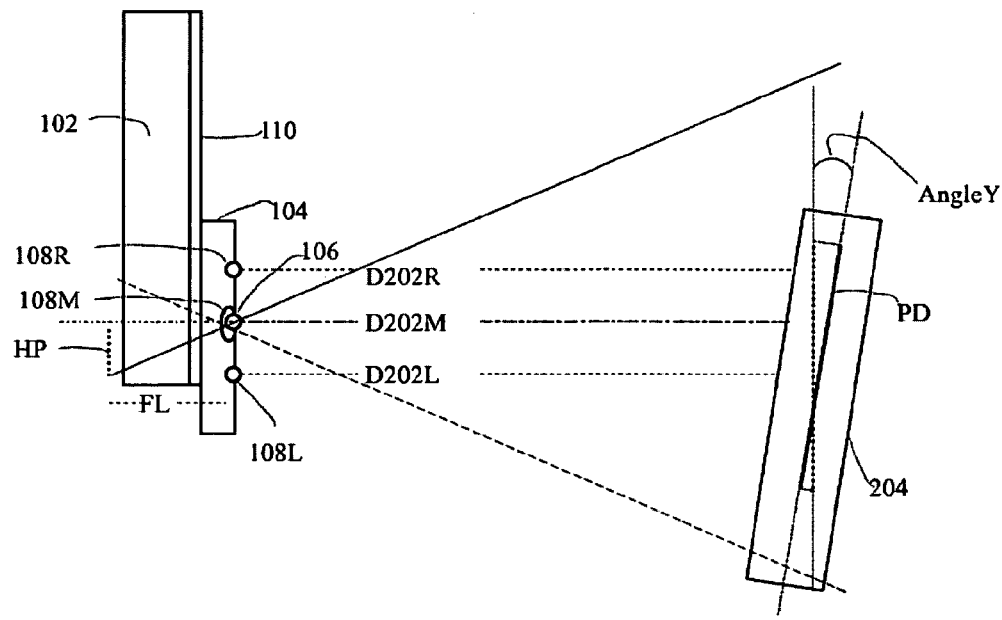
FIG. 5A illustrates a schematic for obtaining a distance measurement and yaw rotation angle.
Figure 5B:
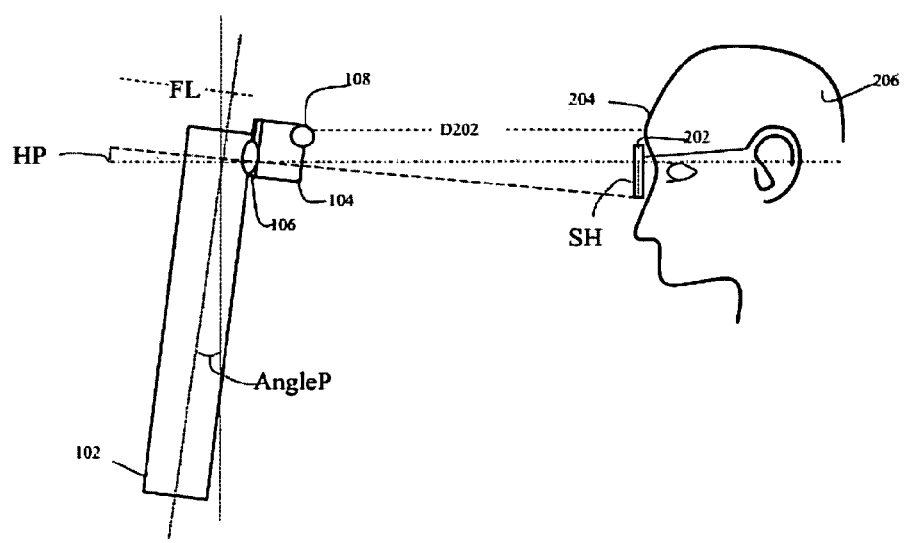
FIG. 5B illustrates a schematic for obtaining a segment height.
Figure 6:
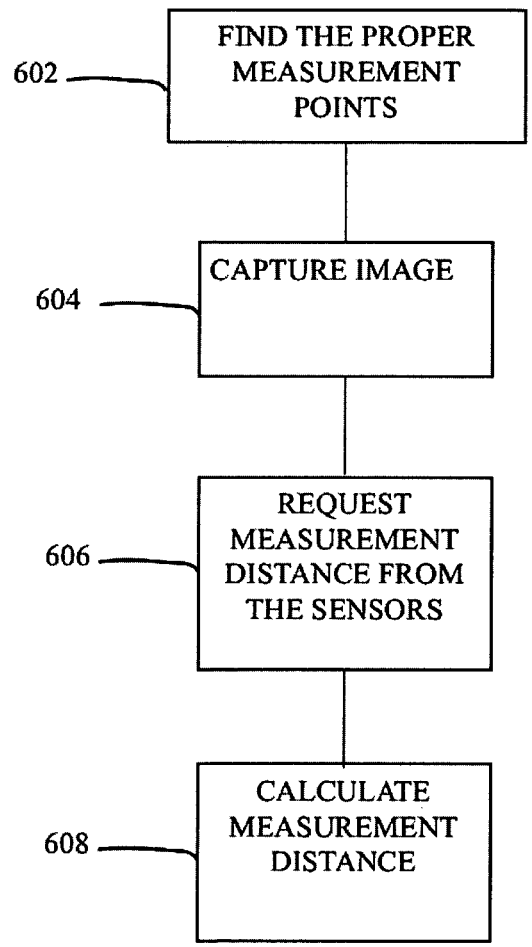
FIG. 6 illustrates flow diagram of method for obtaining distance measurement.

FIGS. 5A and 5B shows method to determine PD, segment Height SH, vertex distance VD, pantoscopic Tilt PT:A method of obtaining a PD according to an illustrative embodiment is indicated in FIGS. 5 and 6. In fact, due to measurement error, there is always non-zero yaw angle AngleY. However, since the proximity sensors 108L, 108M, and 108R always project the forehead 204, a measurement distance D202L, D202M, and D202R can be achieved by getting average reading of three proximity sensors 108L, 108M, and 108R with negligible errors. For example, the measurement distance D202=(D202L+D202M+D202R)/3. In addition, the yaw angle AngleY thus can be estimated based on the known distance D204 and D206 and difference in reading of three proximity sensors D202L, D202M, and D202R. For example, the yaw angle AngleY=tan$^{-1}$ ((D202M−D202L)/D204) or AngleY=tan$^{-1}$VD202R−D202M)/D206). In the illustrative embodiment, the measurement distance D202 and yaw angle AngleY can always be obtained with three proximity sensors 108L, 108M, and 108R, which enable the method reference object free to reduce responsibility of the patient while measuring.

As shown in FIG. 5A, the image of the forehead captured by the digital camera 106 of the mobile device 102 is scaled to the actual dimension of the forehead 204 of the patient head 206. The scale factor is calculated based on the relationship between the focal length FL of the digital camera 106 and the distance D202 that is measured from the digital camera 106 to the patient head 206. The microprocessor of the mobile device 102 thus can re-construct the actual dimension of any object based on number of pixels PP of the captured image.

One example of obtaining pupillary distance PD is described following: (1) the image processing algorithms determine the position of two pupils from the captured image; (2) the image processing algorithm counts number of pixels PP between these two pupils; (3) the processor estimate the actual pupillary distance PD=(PP×D202)/FL. In the illustrative embodiment, the error correction algorithm is also implement when the forehead 204 is not parallel to the array of proximity sensors 108. In such case, the correction formula may be used, wherein the actual pupillary distance PD=(PP× D202)/FL/cos(AngleY).

Another example of obtaining segment height (SH) is described in FIG. 5B: (1) the patient wear a selected frame or a pair of glasses; (2) the image processing algorithms determine the position of two pupils and the location of the frame; (3) the processor estimates the segment height in term of number of pixels from the pupil and the bottom of the frame; (4) the processor re-constructs the actual segment height based on the number of pixels, focal length FL and measurement distance D202. In the illustrative embodiment, the error correction algorithm is also applied for the measurement of the segment height SH if the pitch angle AngleP measured by the gyroscope sensor of the mobile device 102 is non-zero.

The measurement method may be utilized to obtain vertex distance and pantoscopic tilt for binocular PD measurement using additional side images of the patient wearing a selected frame. As illustrated, the measurement is carried out following: (1) the patient wear a selected frame or a pair of glasses; (2) a side image and measurement distance D202 are obtained by the digital camera 106 and the array of proximity sensors 108, respectively; (3) the image processing algorithms determine the locations of frame and the patient's eyes; (4) the processor estimated the number of pixels for vertex distance that is the distance between the frame and the patient's eyes in the side image, and the pantoscopic tilt angle that is the angle of the frame and the vertical line; (5) the processor re-construct the actual vertex distance VD based on the estimated vertex distance in term of number of pixel, the measurement distance D202, the focal length FL; (6) error correction algorithms are utilized to assist the processor to re-calculate the actual pantoscopic tilt angle PT if the roll angle AngleR measured by the gyroscope sensor of the mobile device 102 is non-zero.

FIG. 6 illustrates flow diagram of method for obtaining a distance measurement D202 and a yaw angle AngleY. In the first step 602, the measurement device 104 continuously send information of distance measurement of the middle proximity sensor 108M. The coarse measured distance D202M by the middle proximity sensor 108M assists user to find the proper measurement point. The step guarantee that the distance D202M between the measurement device and the patient face is in the range from 100 mm to 130 mm. Once the mobile device find the proper measurement point, its processor allows to capture image of the patient in the step 604. In the illustrative embodiment, the mobile device 102 is configured to send request to the measurement device 104 to obtain information of all proximity sensors 108. This requesting step 606 is executed right after the digital camera captures the images. Finally, the processor of the mobile device 102 will estimate the measurement distance D202 by averaging all reading values from the proximity sensors 108. In such calculating step 608, the yaw angle AngleY is also estimated based on the difference in reading values of the left and right proximity sensors 108L and 108R.

Figure 7:
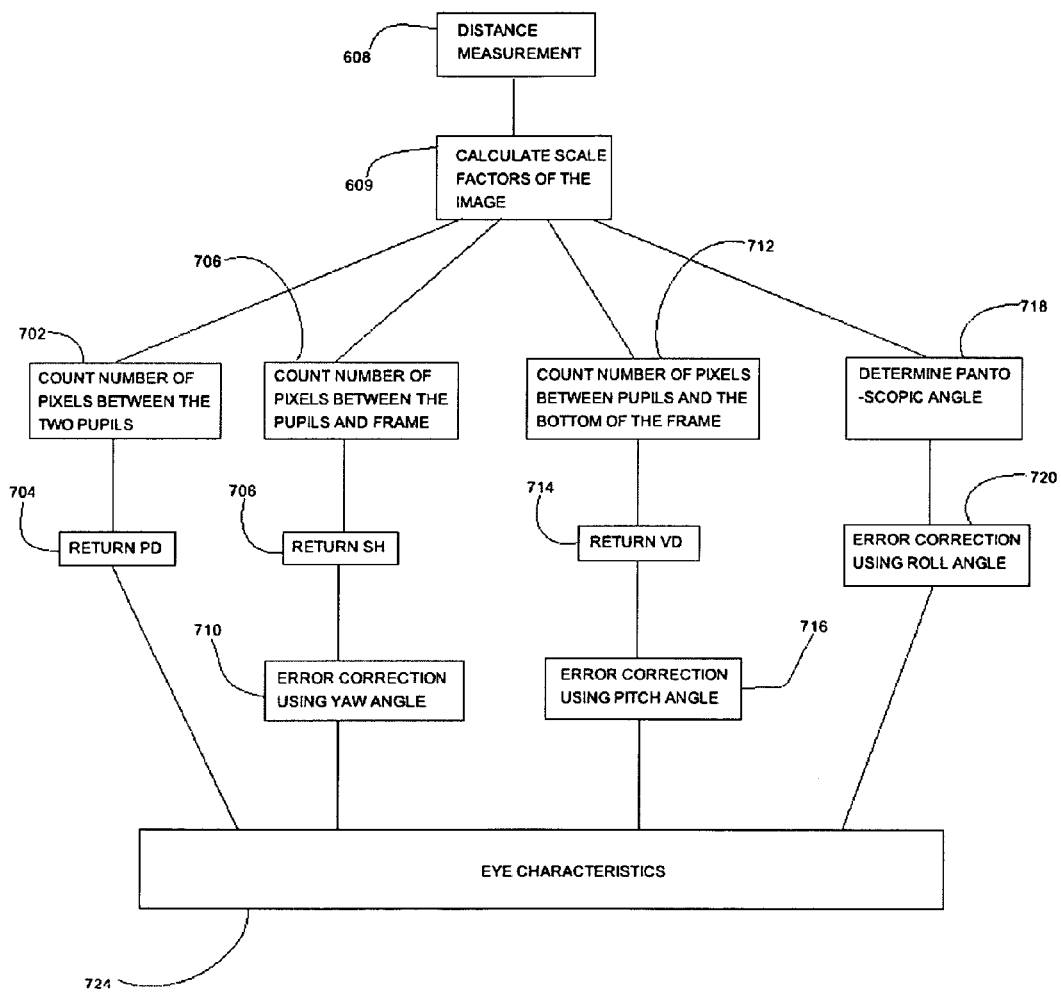
FIG. 7 is a block diagram of an eye characteristic measuring system in accordance with an embodiment of the present system.

FIG. 7 is a block diagram of a eye characteristic measuring system in accordance with an embodiment of the present system. In an illustrative embodiment, the distance measurement D202 obtained in the step 608 is acquired by the array of proximity sensors. Using information of the focal length FL, the step calculate scale factors 609 will return the scale factors which is illustrating the relationship of the captured image in pixel and the actual face in millimeter.

The pupillary distance PD is determined based on number of pixel between the centers of two pupils in the front image counted by the processor of the mobile device 102, in the step 702. The pupillary distance PD is returned by scaling such number of pixels with the measurement distance D202 in the step 704.

The segment height SH is determined by number of pixels between the pupil and the bottom of frame in the front image. In the step 706, the processor utilizes image processing algorithm to find the coordination of the bottom of the frame and the pupils. The number of pixels measured by the step 706 is scaled with the measurement distance D202 to return a segment height SH in the step 708. Error correction using the yaw angle AngleY is applied in the step 710.

The vertex distance VD is determined by number of pixels between the pupil and the frame in the side image. The distance measurement D202 is obtained again while capturing the side image. In the step 712, the processor utilizes image processing algorithms to track the frame 202 and the patient head 206. The processor of the mobile device 102 return actual vertex distance VD, which is proportional to such number of pixels and the distance measurement D202, in the step 714. Error correction using the pitch angle AngleP is applied in the step 716.

The pantoscopic angle PA is determined by the image processing algorithms analyzing the side image. The contour of the frame is tracked and PA is measured versus the vertical line in the step 718. Error correction using the roll angle AngleR is also applied in the step 720.

Figure 8:
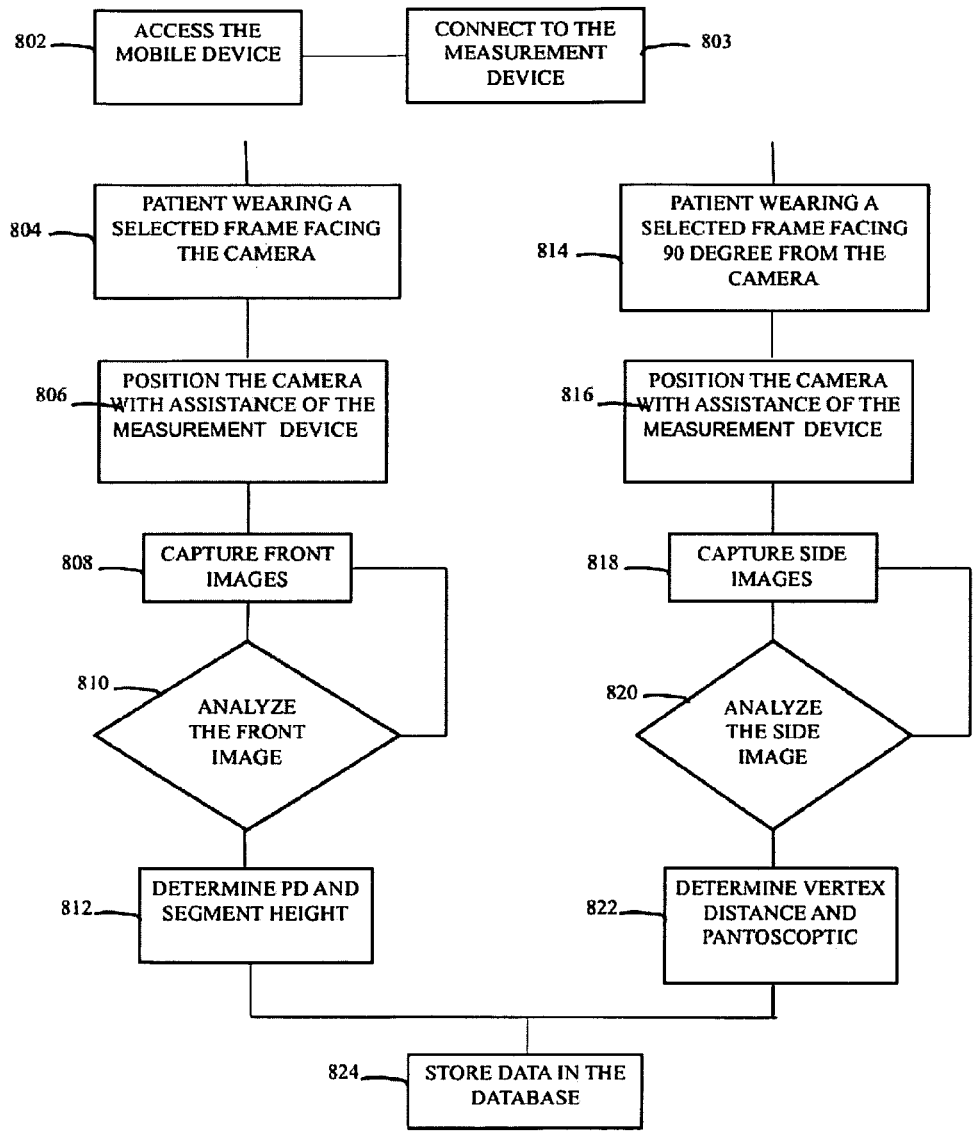
FIG. 8 depicts a flow chart that generally illustrates steps performed by an eye characteristic measuring module.

FIG. 8 depicts a flow chart that generally illustrates steps performed by a particular embodiment. In the step 802, the user accesses the mobile device and activates an application that support the measurement. The application is configured to allow the mobile device to advertise and connect to the measurement device in the step 803. Once the communication between the mobile device and the measurement device is established, the application allow the user to choose different modes of measurement.

If the user want to determine monocular PD and/or binocular PD, the image of front face of the patient needs to be acquired. In the step 804, the patient is required to face the camera and/or wear a selected frame if the patient decides to buy one. Next, the user will position the camera in front of the patient face. In this step 806, the measurement device continuously transmit information to the mobile device that help the user to locate the mobile device in a proper range, which the distance from the patient is from 100 mm to 130 mm. Once the measurement system is within the proper range, the application of the mobile device is configured to allow the user to capture the picture in the step 808. The captured image is used to analyze by the processor of the mobile device in the step 810. Image processing algorithms will determine the validity of the capture images and decide whether it is necessary to re-take another picture. If the capture image is satisfy requirements, the processor calculate the monocular and/or binocular PD in the step 812. In this step, segment height SH of the selected frame is also estimated if required.

If the user want to determine vertex distance and pantoscopic angle of a selected frame, the image of side face of the patient needs to be acquired. In the step 814, the patient is required to face 90 degree from the camera and wear the selected frame. Next, the user will position the camera toward the side of the patient. In this step 816, the measurement device continuously transmit information to the mobile device that help the user to locate the mobile device in a proper range, which the distance from the patient is from 100 mm to 130 mm. Once the measurement system is within the proper range, the application of the mobile device is configured to allow the user to capture the picture in the step 818. The captured image is used to analyze by the processor of the mobile device in the step 820. Image processing algorithms will determine the validity of the capture images and decide whether it is necessary to re-take another picture. If the capture image is satisfy requirements, the processor calculate the vertex distance VD and pantoscopic angle PA in the step 822.

Once the measurement finishes, the data of the selected frame, pupillary distance PD, segment height SH, vertex distance VD and pantoscopic angle PA could be encrypted and stored in the database, the step 824. The information associated with the patient's personal information will be uploaded to Internet Cloud and shared with the ophthalmic laboratory if needed. The historical data is necessary for the doctors and/or users for the next measurement.

Figure 9:
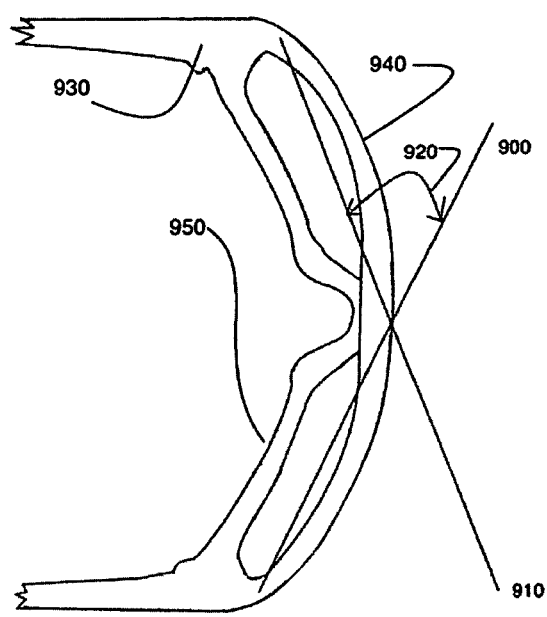
FIG. 9 depicts an image captured of, top view of an eye wear frame resting on a table for wrap angle measurement.

FIG. 9 depicts an embodiment of the measurement method for wrap angle (WA). The steps involve resting the frame 930 on a flat surface with top side of the frame facing up as if worn of face. 940 is the top left rim of the frame and 950 its bottom right rim surface. Take a picture using camera 106 of mobile device 102 with the camera looking down in a substantially small vertical angle with mobile device substantially parallel to the flat surface. The mobile device now presents the frame image on the mobile device screen. User can draw line 910 on software screen such that it passes through the extreme left point where the lens touches the rim 940 and with second point being extreme right point where the lens touches the rim 940. Similarly line 900 is drawn using the right rim lens points. The software automatically calculates the WA 920. The same result is obtained when you use the bottom rims to draw the lines. In another embodiment the frame top image is not captured, but lines drawn on live feed of the image.

In another embodiment of the invention, an external camera can make the measurement and a personal computer can calculate the WA. In another embodiment of the invention, the software can automatically capture image when mobile device 106 is substantially horizontal and draw lines and calculate wrap without user taking picture and drawing the lines.

In conclusion many modifications and other embodiments of the invention will come to mind to one skilled in the art to which this invention pertains having the benefit of the teachings presented in the foregoing descriptions and the associated drawings. For example, as will be understood by one skilled in the relevant field in light of this disclosure, the invention may take form in a variety of different mechanical and operational configurations. For example, the measurement device described in this embodiment may include different types or number of sensors, such as, acoustic sound sensors, magneto-inductive displacement sensors, and/or proximity capacitive/inductive sensors, etc. Therefore, it is to be understood that the invention is not to be limited to the specific embodiments disclosed and that the modifications and other embodiments are intended to be included within the scope of the appended exemplary concepts. Although specific terms are employed herein, they are used in a generic and descriptive sense only and not for the purposes of limitation.

What is claimed is:

1. An apparatus and method for contactless measurement of, one or more, eye and eyewear characteristics, without one or more known reference dimensions for scaling measurements, comprising:

a mobile device itself comprising a digital camera, a wireless transceiver, an accelerometer sensor and a gyroscope sensor;

a measurement device consisting array of distance reporting proximity sensors, a microcontroller, a power supply and a Bluetooth low-energy transceiver to communicate with said wireless transceiver of said mobile device;

said measurement device configured to receive control signals from said mobile device when its camera being activated and send information of measured distance to said mobile device for calculation of eye characteristics;

software running on the said measurement device that measures and responds to queries from the said mobile device;

method of running a software on the said mobile device such that it provides a user interface and co-ordinates:
user interaction with measurement setup;
providing live and dynamic guiding lines, advice text and capture points positioning and measurement out of range conditions on said user interface to ensure capture of patient face and frame image correctly;
capturing patient face and frame image from front side;
capturing a second patient face and frame image from the side;
capturing an optional third image of the frame placed on a flat surface;
acquiring said distance measurements from the said measurement device wirelessly;
calculating said characteristics from said distance measurements and distances and angles in the images captured by the said mobile device;

application of scaling;

application of error corrections to said measurements based on said accelerometer and gyroscopes data;

presentation of said measurement results on user interface;

providing ability to manually adjust measurement lines and angles determined and drawn on user interface by the said mobile device;

and uploading of said measurement results to a remote server or computer.

2. The system of claim 1, wherein the said proximity sensor is a time-of-flight laser sensor to minimize effect of ambient light and texture of the said face on the said distance measurements.

3. The system of claim 1, wherein the proximity sensor is a time-of-flight ultrasonic sensor to minimize effects of surface absorption at the said face on the said distance measurements.

4. The system of claim 1, wherein said measurement device is removably attached to said mobile device using a mechanical adaptive clip comprising of:

A horizontal slider connected to a top strap and said measurement device;

A bottom strap having a mechanical clip; and the said mechanical clip body, wherein could lock relative moving between said top strap and said bottom strap along said horizontal slider.

5. The system of claim 1, wherein said mobile device requests said measurement device to send measured distance and yaw angle when said mobile device captures front or side images of the said face.

6. The system of claim 1, wherein said mobile device calculates pupillary distance based on number of pixels counted on said front image and scale factors based on distance information acquired by said measurement device and a focal length of said digital camera.

7. The system of claim 1 further estimates segment height, wherein said patient wears a pair of bifocal glasses.

8. The system of claim 1, wherein vertex distance and pantoscopic angle are estimated based on said measured distance, a focal length when said digital camera takes picture and number of pixels measured on said side image.

9. The system of claim 1, measures the wrap angle of the frame from the said image captured from the top; the smaller angle of the two lines drawn by the user on the said user interface, intersecting the planes of left and right lenses in the eyewear rims, gives the wrap angle.

10. The system of claim 1, wherein said array of proximity sensors of said measurement device comprises of at least three sensors to detect distance to the face of a patient at multiple points so as to calculate a yaw, roll and pitch angles of said face so as to apply better error correction due to errors in the captured image on the said mobile device due to the said roll, pitch and yaw angles.

11. The system of claim 1, wherein said accelerometer and gyroscope sensors of said mobile device measures relative pitch and roll angles of the said device to provide additional error correction in the captured image on the said mobile device due to the its own roll, pitch and yaw angles.

12. The system of claim 1, wherein a plurality of cameras are external to the said mobile device, they capture images on command from said mobile device and sends it the images wirelessly or through USB cables; this eliminates need for multiple image capture from the said mobile device camera.

13. The measurements of claims 6, 7, 8, or 9 are automatically computed without user input by the computer vision software component in the said software of the said mobile device of claim 1.

14. The system of claim 1, wherein the said mobile device and its software is replaced by a generic personal computer and similar software.

15. The system of claim 1, wherein the said measurement device takes over the said tasks of the said mobile device and the said software.

\* \* \* \* \*